United States Patent
Lecoeuvre

(10) Patent No.: US 12,186,160 B2
(45) Date of Patent: Jan. 7, 2025

(54) DRESSING WITH IMPROVED FLUID DISTRIBUTION

(71) Applicant: ADVANCED SILICONE COATING, Pusignan (FR)

(72) Inventor: Jean-François Lecoeuvre, Sorbiers (FR)

(73) Assignee: ADVANCED SILICONE COATING, Pusignan (FR)

( * ) Notice: Subject to any disclaimer, the term of this patent is extended or adjusted under 35 U.S.C. 154(b) by 350 days.

(21) Appl. No.: 17/618,661

(22) PCT Filed: Jul. 1, 2020

(86) PCT No.: PCT/EP2020/068579
§ 371 (c)(1),
(2) Date: Dec. 13, 2021

(87) PCT Pub. No.: WO2021/001454
PCT Pub. Date: Jan. 7, 2021

(65) Prior Publication Data
US 2022/0354703 A1 Nov. 10, 2022

(30) Foreign Application Priority Data
Jul. 2, 2019 (FR) ..................................... 1907343

(51) Int. Cl.
*A61F 13/0203* (2024.01)
*A61F 13/00* (2024.01)
*A61F 13/0246* (2024.01)

(52) U.S. Cl.
CPC ...... *A61F 13/0223* (2013.01); *A61F 13/0226* (2013.01); *A61F 13/0253* (2013.01);
(Continued)

(58) Field of Classification Search
CPC .... A61F 13/00; A61F 13/0246; A61F 13/025; A61F 13/0203; A61F 13/00008;
(Continued)

(56) References Cited

U.S. PATENT DOCUMENTS

| 5,632,731 A | 5/1997 | Patel |
| 10,076,449 B2 * | 9/2018 | Allen ...................... A61F 13/05 |
| 2010/0292626 A1 | 11/2010 | Gundersen et al. |

FOREIGN PATENT DOCUMENTS

| FR | 2974005 A1 * | 10/2012 | ............. A61F 13/02 |
| WO | 9307841 A1 | 4/1993 | |

(Continued)

OTHER PUBLICATIONS

FR 2974005 A1 machine translation (Year: 2012).*
(Continued)

*Primary Examiner* — Caitlin A Carreiro
(74) *Attorney, Agent, or Firm* — Maier & Maier, PLLC

(57) ABSTRACT

A dressing including a film which is impermeable to fluids and permeable to water vapor, and the entire surface of which is covered by a perforated reinforcement coated with a medically acceptable adhesive which is the same or different on each of the faces thereof, the face opposite to the face in contact with the impermeable film of an adhesive being partially covered by an absorbent pad, The dressing further includes a layer for distributing the fluids which is positioned between the impermeable film and the perforated reinforcement.

14 Claims, 2 Drawing Sheets

(52) U.S. Cl.
CPC ............... *A61F 2013/00659* (2013.01); *A61F 2013/00744* (2013.01); *A61F 2013/00863* (2013.01)

(58) Field of Classification Search
CPC .. A61F 13/00021; A61F 13/022; A61F 13/02; A61F 13/0223; A61F 13/0226; A61F 13/0253; A61F 13/0206; A61F 2013/00659; A61F 2013/00744; A61F 2013/00863; A61F 2013/00676; A61F 2013/00719; A61F 2013/00876; A61F 2013/00868; A61F 2013/00089; A61F 2013/00238; A61F 2013/00246; A61F 2013/00251; A61F 2013/00255; A61F 2013/00259; A61F 2013/00582; A61K 9/70; A61L 15/00; A61L 15/58; A61L 26/00

USPC ...... 602/41–45, 47, 52, 54, 58, 59; 424/445, 424/448; 604/304, 307
See application file for complete search history.

(56) References Cited

FOREIGN PATENT DOCUMENTS

| WO | WO-2009081134 A1 * | 7/2009 | ......... A61F 13/0203 |
| WO | 2012140377 A1 | 10/2012 | |

OTHER PUBLICATIONS

International Search Report (with English translation) and Written Opinion (with Machine translation) issued on Sep. 29, 2020 in corresponding International Application No. PCT/EP2020/068579; 16 pages.

* cited by examiner

[Fig. 1]
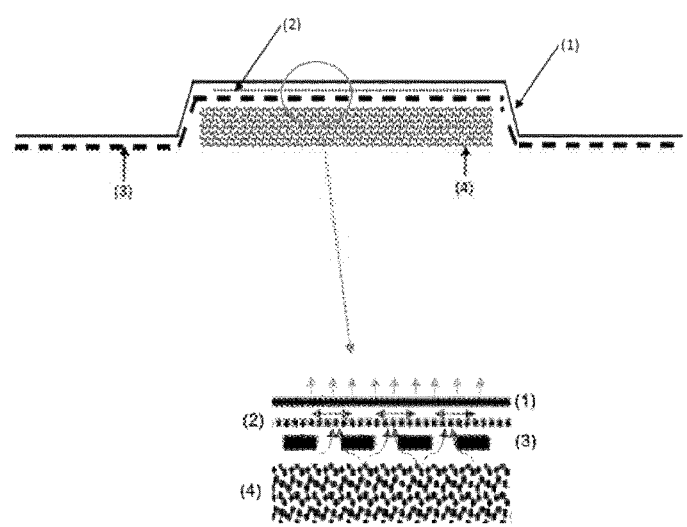
[Fig. 2]
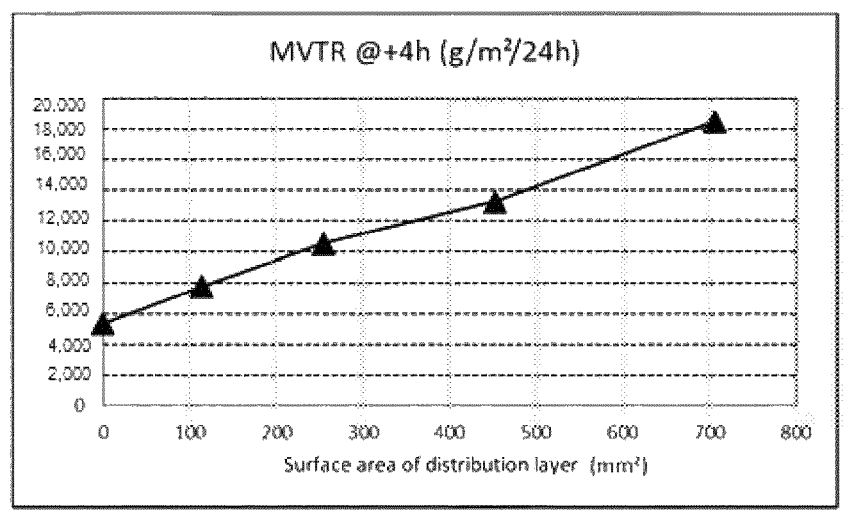

[Fig. 3]
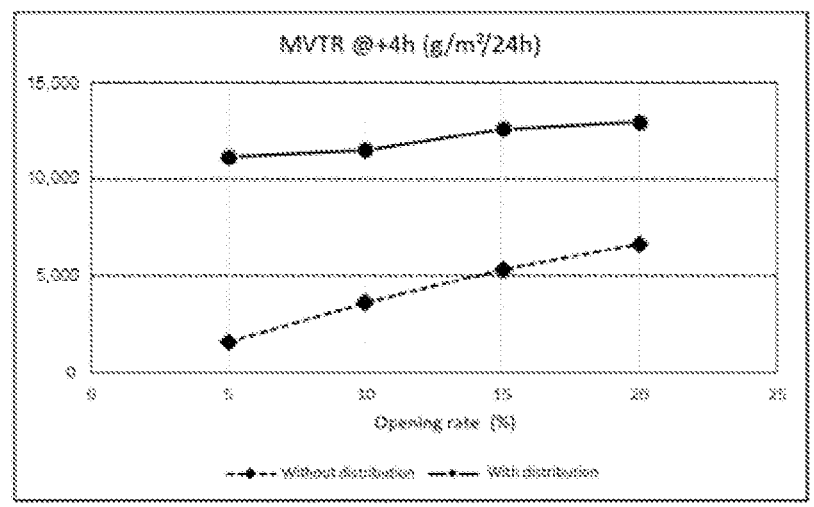

DRESSING WITH IMPROVED FLUID DISTRIBUTION

TECHNICAL FIELD OF THE INVENTION

The present invention relates to an absorbent dressing for treating chronic or acute wounds, said dressing comprising a film which is impermeable to fluids and permeable to water vapour, a perforated reinforcement, an absorbent pad and a fluid distribution layer inserted between said impermeable film and said perforated reinforcement.

BACKGROUND

Absorbent dressings used for treating chronic or acute wounds generally consist of an absorbent pad sandwiched between a breathable impermeable protective film and an open interface layer coated on at least one of the faces thereof with a silicone adhesive, to prevent direct contact between the pad and the wound.

Other dressings comprise an absorbent pad intended to be directly in contact with the wound. Indeed, direct contact between the pad and the wound can induce a beneficial therapeutic effect. However, in the absence of the open interface coated with silicone, this type of dressing comprises an adhesive perimeter, commonly known as a border, projecting from the pad and used for holding in place on the patient.

For example, US patent application 2010/0292626 describes a dressing wherein only the border is coated with silicone adhesive and the absorbent pad is in direct contact with the wound. To produce the dressing, a polyurethane film coated with silicone adhesive is cut to the shape of the border, then bonded to a breathable impermeable substrate film by means of an acrylic adhesive. The production of this dressing is complex (steps of cutting, centring the components) and gives rise to a significant loss of the material coated with silicone adhesive to produce the slot accommodating the pad and produce the adhesive border.

The application WO2012140377 describes another dressing including an absorbent pad intended to be in direct contact with the wound. This pad is bonded to an adhesive, breathable, impermeable substrate complex. The adhesive, breathable, impermeable substrate consisting of the assembly of an open knit textile weave, coated on the two faces thereof with silicone adhesive pasted onto a breathable impermeable polyurethane film. The presence of this complex makes it possible to improve the rigidity of the dressing and facilitates the use thereof. Moreover, the surface portions of polyurethane film accessible next to the porosities of the textile weave have a high breathability. On the other hand, the breathability is substantially limited in the solid zones of the textile weave. A person skilled in the art must therefore find a compromise between breathability and adhesive power, both dependent on the ratio of the open surface area over the total surface area (opening rate) with antinomic effects. Thus, a high opening rate will favour high breathability to the detriment of the adhesive power.

Alternatively, the open textile weave coated with silicone adhesive gel can be replaced by a thermoplastic film, coated with adhesive on both faces thereof, perforated and pasted to a breathable, impermeable polyurethane film. In this case, for a given opening rate and a given breathability, it is possible to improve the adhesive power of the dressing more easily through the choice of a high-adhesive-performance silicone adhesive and through the quantity of silicone adhesive deposited. It remains nonetheless necessary to find a compromise between adhesive power and breathability.

Another alternative, described in the patent EP2231088B1, consists of replacing the adhesive open textile weave and the double-sided adhesive film by a thermoplastic unitary net coated on both faces thereof with adhesive.

However, all these alternatives have the same drawback which is that any variation of the opening rate, whether via a reduction in the dimensions of the holes, or through the presence of poorly opened or unopened holes, results in a significant loss of breathability. The latter can impair the wound treatment or care function, or even induce tissue maceration through excess moisture.

Moreover, devising a dressing in which the breathability level is very high, while ensuring satisfactory adhesion of heavy pads once filled with exudates, and particularly in the case of so-called "superabsorbent" pads can sometimes prove to be impossible.

Therefore, there is a need for a dressing with a central absorbent pad which is impermeable to liquids, which has an adhesive border with high adhesion performances, satisfactory pad adhesion and very high breathability next to the latter. Moreover, this dressing must be easy to manufacture, without unnecessary losses of silicone adhesive-coated substrate.

SUMMARY

Thus, the present invention particularly relates to a dressing comprising:
- a film which is impermeable to fluids and permeable to water vapour, and the entire surface of which is covered by,
- a perforated reinforcement coated with a medically acceptable adhesive which is the same or different on each of the faces thereof, the face opposite to the face in contact with said impermeable film being partially covered by,
- an absorbent pad,
remarkable in that said dressing further comprises a fluid distribution layer inserted between said impermeable film and said perforated reinforcement.

In the framework of the present invention, the term "be covered" is intended to mean that a first layer of the dressing according to the invention is completely or partially plumb with a second layer of the dressing according to the invention. The term cover does not imply that said layers are in direct contact.

In the framework of the present invention, the term "perforated" is intended to mean that said reinforcement is not continuous, but has holes traversing either side thereof.

In the framework of the present invention, the term "absorbent" is intended to refer to the ability of a material to retain a certain quantity of water inside the structure thereof. According to a preferred embodiment of the invention, a material is referred to as "absorbent" when it is capable of retaining in the structure thereof a liquid mass greater than 1 g per 100 cm$^2$ of material and more preferably 50 g per 100 cm$^2$ of material (test performed as per the NF EN 13729-1 standard para. 3.2).

In the framework of the present invention, the term "distribution layer" is intended to refer to any layer wherein a liquid will be capable of diffusing horizontally and vertically.

Indeed, it was surprisingly found that the presence of a distribution layer between the perforated reinforcement and the impermeable film made it possible to increase the breathability of this type of dressing substantially compared to dressings according to the prior art.

The distribution layer enables the transfer of the exudates over the entire surface thereof in contact with the film. In a first stage, the exudates only pass through the porosities of the perforated reinforcement, then are distributed horizontally and vertically thanks to the action of the distribution layer. The entire surface of the film which is impermeable to fluids and permeable to water vapour located above the distribution layer then becomes available to allow water vapour to pass through. This results in a very substantial increase in the breathability of the dressing in this zone. Consequently, the breathability next to the pad is not limited by the opening rate of the perforated reinforcement bonded to the film which is impermeable to fluids and permeable to water vapour. Thus, it is possible to use perforated reinforcements with a high adhesive power to obtain a border with high adhesive performances for a satisfactory hold of the dressing on the patient's skin, and a high adhesive performance next to the pad helping ensure satisfactory adhesion thereof, even once filled with exudates.

According to a preferred embodiment of the invention, said film which is impermeable to fluids and to water vapour is made of polyurethane.

According to a preferred embodiment of the invention, said perforated reinforcement is coated on the face thereof in contact with said impermeable film with a medically acceptable adhesive and on the other face thereof with an adhesive silicone gel.

According to a preferred embodiment of the invention, said film which is impermeable to fluids and to water vapour has a thickness between 5 µm and 100 µm and more preferably between 10 µm and 40 µm.

According to a preferred embodiment of the invention, said film which is impermeable to fluids and to water vapour has an MVTR breathability to water vapour in liquid contact, measured after 4 hours of tests as per the EN 13726-2:2002 standard, between 500 $g/m^2/24$ h and 60,000 $g/m^2/24$ h and more preferably between 10,000 $g/m^2/24$ h and 30,000 $g/m^2/24$ h.

According to a preferred embodiment of the invention, said fluid distribution layer extends over the entire surface of the pad.

According to another preferred embodiment of the invention, said fluid distribution layer extends over a surface less than that of the pad.

According to another preferred embodiment of the invention, said fluid distribution layer extends over the entire surface of the pad and beyond the surface of the pad.

According to a preferred embodiment of the invention, said fluid distribution layer is composed of a woven or knit textile, a nonwoven material, or an absorbent material.

According to a preferred embodiment of the invention, said fluid distribution layer can comprise additives such as antimicrobial, anti-odour products, or any other additional additives.

According to an even more preferred embodiment of the invention, said woven or knit textile is composed of natural fibres or of synthetic fibres.

According to an even more preferred embodiment of the invention, said nonwoven textile is composed of a material chosen in the group comprising polyethylene, polypropylene, polyester, polyamide and mixtures thereof.

According to an even more preferred embodiment of the invention, said absorbent material is composed of a material chosen in the group consisting of hydrophilic polyurethane, carboxymethylcellulose fibres, sodium polyacrylate, sodium alginate, carboxymethylcellulose, sodium polyacrylate, sodium alginate, derivatives thereof and mixtures thereof.

According to a preferred embodiment of the invention, said perforated reinforcement is a perforated knit, a unitary net made of thermoplastic material, a perforated film or a perforated nonwoven.

According to an even more preferred embodiment of the invention, said open knit consists of synthetic fibres such as polyethylene, polypropylene, polyamide or polyester, and more preferably of polyester.

According to an even more preferred embodiment of the invention, said unitary net made of thermoplastic material consists of a material chosen in the group consisting of polyethylene, polypropylene, polyamide, polyurethane and mixtures thereof.

According to an even more preferred embodiment of the invention, said film consists of polyurethane or of copolyester.

According to a preferred embodiment of the invention, said adhesive is a hydrogel, a pressure-sensitive adhesive (PSA) or a silicone-based adhesive and even more preferably an adhesive silicone gel.

According to a preferred embodiment of the invention, the total weight of adhesive on all of both faces of the perforated reinforcement is between 30 $g/m^2$ and 500 $g/m^2$ and more preferably between 100 $g/m^2$ and 300 $g/m^2$.

According to a preferred embodiment of the invention, the perforated reinforcement has an opening rate between 5% and 50% and more preferably 10 and 30%.

According to a preferred embodiment of the invention, the absorbent pad consists of a material chosen in the group consisting of hydrophilic polyurethane foams, absorbent nonwoven materials based on carboxymethylcellulose fibres or sodium alginate, composites based on porous nonwoven materials comprising sandwiched absorbent materials and sachets containing absorbent materials.

BRIEF DESCRIPTION OF THE FIGURES

FIG. 1 shows a sectional view of an embodiment of a dressing according to the invention.

FIG. 2 shows the progression of the breathability of an embodiment of a dressing according to the invention as a function of the surface area of the distribution layer.

FIG. 3 shows the progression of the breathability of an embodiment of a dressing according to the invention as a function of the opening rate of the perforated reinforcement.

DETAILED DESCRIPTION

The preferred embodiment of the dressing according to the invention described in FIG. 1 comprises:
 a film 1 which is impermeable to fluids and permeable to water vapour, and the entire surface of which is covered by,
 a perforated reinforcement 3 coated on the face thereof in contact with said impermeable film with an adhesive and on the other face thereof with an adhesive silicone gel, the latter face being partially covered by,
 an absorbent pad 4,
 a fluid distribution layer 2 inserted between said impermeable film 1 and said perforated reinforcement 3.

The surface area of said dressing, the shape thereof, the surface area of the border and of the absorbent pad 4 are dependent on the type of wounds to be treated. A person skilled in the art is capable of defining, for each need, the optimum surface areas of each of the components.

The surface area of the border can be increased to improve the ability of the dressing according to the invention to adhere to the patient's skin.

The adhesiveness of the perforated reinforcement 3 can also be modified by varying:
- the dimension of the holes (length, width or diameter) which can vary between 0.1 mm and 8 mm, preferably between 1.0 mm and 3 mm,
- the distribution thereof in relation to each other (e.g. positioning at 45°, at 60° or at) 90°,
- the density thereof in number per unit of surface area, defined by an opening rate represented by the ratio between the open surface area relative to the total surface area.

Usually, the surface area of the distribution layer 2 is equivalent to that of the absorbent pad 4 placed next to the latter. However, said distribution layer 2 can advantageously extend beyond said absorbent pad 4 in order to improve the breathability of the dressing at the border and discharge the moisture released by sudation at the border.

Said distribution layer 2 can also have a surface area less than that of the pad 4 so as to obtain a breathability that is certainly sufficient, but not excessive so as not to risk drying the bed of the wound.

The different layers of the dressing according to the invention can be produced and assembled by any means known to a person skilled in the art.

Preferably, the film which is impermeable to fluids and permeable to water vapour 1 can be obtained by blown film extrusion, by flat extrusion, by solvent-phase liquid coating on a substrate based on paper or synthetic film both coated with an anti-adherent layer.

Preferably, the perforated reinforcement 3 coated on both faces thereof with one or more medically acceptable adhesives can be obtained by coating both faces, for example by coating or steeping in a bath, of a perforated knit type open textile or a unitary net made of thermoplastic material, or perforating a film of a nonwoven previously coated on both faces thereof with one of more medically acceptable adhesives. The open knit can be obtained by so-called "warp" knitting. The unitary material net can be obtained by extrusion casting followed by hot stretching after perforation. The film can be obtained by blown film extrusion, by flat extrusion, or by liquid coating in solvent phase on a carrier. The nonwoven can be obtained by so-called melt blown or spunbound technology if the selected fibres are thermoplastic or by so-called spunlace technology in the case of nonwoven materials containing non-thermoplastic fibres.

All the materials cited in the present application can be advantageously combined with functional agent for treating the wound such as antimicrobial, disinfectant, and-odour, wound treatment activating and/or detergent products.

A corona treatment as described by the applicant in the document WO 2015044535 A1 can be advantageously applied to the silicone adhesive on the surface intended to be bonded thereto (pad 4 and/or breathable impermeable film 1)

EXAMPLES

Example 1: Demonstration of the Specific Effect of a Distribution Layer 2 on Breathability In order to demonstrate the effect of the distribution layer 2 on the breathability of a construction according to the invention, the applicant constructed assemblies comprising

- a film which is impermeable to fluids and permeable to water vapour 1, and the entire surface of which is covered by,
- a perforated reinforcement 3 coated on the face thereof in contact with said impermeable film,
- a fluid distribution layer 2 inserted between said impermeable film and said perforated reinforcement (except for control sample).

The perforated reinforcement 3 was a polyurethane film, coated on one face with acrylic adhesive and on the other face with silicone adhesive, then perforated and assembled with polyurethane films 1 with and without (control) insertion of a distribution layer 2.

In the assembly obtained, assembled disks of overall diameter 42 mm were cut, optionally comprising a diffusion disk, bonded at the centre thereof, of diameter arbitrarily defined as 24 mm, then subjected to the breathability measurement test in liquid contact (MVTR) as per the EN 13726-2:2002 period for a 4 h duration.

The perforated reinforcement 3 was manufactured by the applicant under the reference Acrysil 150 703731, perforated with holes at 60°, diameter 2.4 mm and 15% opening rate.

The distribution layers 2 evaluated are:
- a 45 g/m$^2$ polyester nonwoven (reference Sontara Spunlace Style 8000 distributed by Jacob Holm Industries).
- a polyurethane foam of thickness 1.5 mm (reference Vilmed 6217 manufactured by Freudenberg).
- an absorbent nonwoven (reference Vilmed M1556 manufactured by Freudenberg).

The films which are impermeable to fluids and permeable to water vapour 1 used were:
- A film of thickness 15 μm (reference Inspire 2350, manufactured by Transcontinental Advanced Coating Ltd).
- A film of thickness 30 μm (reference Inspire 2301, manufactured by Transcontinental Advanced Coating Ltd).

The MVTR breathability observed for each of these constructions is stated in [Table 1] below.

TABLE 1

| | Control assembly (with no diffusion layer) | Assembly with polyester nonwoven | Assembly with polyurethane foam | Assembly with absorbent nonwoven |
|---|---|---|---|---|
| PU film 15 μm | 5442 g/m$^2$/24 h | 14224 g/m$^2$/24 h | 14058 g/m$^2$/24 h | 20839 g/m$^2$/24 h |
| PU film 30 μm | 2945 g/m$^2$/24 h | 7664 g/m$^2$/24 h | 9443 g/m$^2$/24 h | 11448 g/m$^2$/24 h |

It is thus observed, surprisingly, that inserting a diffusion layer 2 between the perforated reinforcement 3 and the film 1, makes it possible to increase, by 160% to 290% depending on the cases, the breathability of the complex.

Even more surprisingly, the breathability increases very substantially if the distribution layer 2 tends to swell on absorbing the liquid (case of Vilmed 6217 foam), then inducing a deformation elongation of the film 1 since it is not bonded; this then results in greater breathability of the film 1 by elongation, increase in the exchange surface area, and reduction in thickness.

Example 2: Demonstration of the Effect of a Distribution Layer 2 on the Breathability of a Dressing According to the Invention The assemblies of example 1 are produced identically on the 15 μm film 1, but an absorbent polyurethane foam disk is bonded to the perforated reinforcement 3, on the silicone adhesive side, to represent the absorbent pad 4.

The absorbent polyurethane foam pad 4 used has a thickness of 2 mm (reference MC F03 manufactured by Advanced Medical Solutions Group Plc).

The assembled disks, of diameter 42 mm, optionally comprising a distribution layer 2 of diameter 24 mm, are subjected to the breathability measurement test in liquid contact (MVTR) as per the EN 13726-2:2002 period for a 4 h duration.

The MVTR breathability observed for each of these constructions is stated in [Table 2] below.

TABLE 2

| | Control assembly (with no diffusion layer) | Assembly with polyester nonwoven | Assembly with polyurethane foam | Assembly with absorbent nonwoven |
|---|---|---|---|---|
| PU film 15 μm | 5414 g/m²/24 h | 13767.6 g/m²/24 h | 11964 g/m²/24 h | 17136 g/m²/24 h |

It is thus observed that adding an absorbent pad 4 reduces the overall MVTR of the dressing slightly, but the effect due to inserting the distribution layer 2 is not cancelled.

Example 3: Effect of the Variation of the Surface Area of the Distribution Layer 2 on the Breathability of a Dressing According to the Invention Assemblies according to example 1 with a 15 μm film 1 were produced by varying the diameter, therefore the surface area of the distribution layer 2.

The distribution layer 2 evaluated was a 45 g/m² polyester nonwoven (reference Sontara Spunlace Style 8000 distributed by Jacob Holm Industries).

The assembled disks, of diameter 42 mm, optionally comprising a distribution layer 2 of variable diameter (12, 18, 24 & 30 mm) were subjected to the breathability measurement test in liquid contact (MVTR) as per the EN 13726-2:2002 period for a 4 h duration.

The results obtained are shown in [FIG. 2].

It is thus observed that the distribution layer 2 fully fulfils its role, the moisture being evaporated over a greater surface area of film 1.

Consequently, it is possible to vary the MVTR breathability by merely varying the surface area of the distribution layer 2. In some cases, it may be desirable to have a maximum breathability to prevent an accumulation of exudates at the wound and thus tissue maceration. On the other hand, in some cases, it is necessary to limit the breathability of the dressing to prevent drying of the wound bed and thus promote wound healing.

Example 4: Effect of the Variation of the Opening Rate of the Perforated Reinforcement 3 on the Breathability of a Dressing According to the Invention Assemblies according to example 1, comprising a 15 μm film 1, were constructed by varying the perforation design of the perforated reinforcement 3 so as to generate perforations having different diameters and opening rates.

Assemblies, of diameter 42 mm, optionally comprising a distribution disk 3 of diameter 24 mm, are subjected to the breathability measurement test in liquid contact (MVTR) as per the EN 13726-2:2002 period for a 4 h duration.

The results obtained are shown in [FIG. 3].

It is observed that, without a distribution layer 2, the breathability remains closely dependent on the opening rate of the perforated reinforcement 3. Conversely, in the presence of the distribution layer 2, the MVTR is virtually stable according to the opening rate and therefore the adhesive power of the dressing according to the invention.

Consequently, unlike the dressing according to the prior art, the dressing according to the invention makes it possible to readily modify the breathability of the dressing without modifying the opening rate of the perforated product and therefore without modifying the adhesive power thereof on the patient. Conversely, it is possible to modulate the adhesive power of the dressing on the skin and/or the absorbent pad 4 on the perforated reinforcement 3 (by modifying the opening rate of the perforated reinforcement 3 and/or the size of the borders) without modifying the overall breathability of the finished dressing.

Additionally, it is thus possible to modulate and optimise the two features of breathability and adhesive power completely independently unlike the dressings of the prior art.

The invention claimed is:

1. A dressing, comprising:
a film which is impermeable to fluids and permeable to water vapour;
a perforated reinforcement covering an entire surface of the film and coated with a medically acceptable adhesive, wherein the adhesive is the same or different on each face of the perforated reinforcement, the perforated reinforcement having a first face in contact with at least a part of the surface of the film;
an absorbent pad partially covering a second face of the perforated reinforcement, the second face being opposite the first face; and
a fluid distribution layer composed of an absorbent material and inserted between the film and the first face of the perforated reinforcement; wherein, when the dressing is affixed to a skin of a patient, the absorbent pad is configured to be disposed closer to the skin than the fluid distribution layer.

2. The dressing according to claim 1, wherein said film which is impermeable to fluids and permeable to water vapour is made of polyurethane.

3. The dressing according to claim 1, wherein said perforated reinforcement is coated on the first face thereof with a medically acceptable adhesive and on the second face thereof with an adhesive silicone gel.

4. The dressing according to claim 1, wherein said film which is impermeable to fluids and permeable to water vapour has a thickness between 5 μm and 100 μm.

5. The dressing according to claim 1, wherein said film which is impermeable to fluids and permeable to water vapour has an MVTR breathability to water vapour in liquid contact, measured after 4 hours of tests as per the EN 13726-2:2002 standard, between 500 g/m²/24 h and 60,000 g/m²/24 h.

6. The dressing according to claim 1, wherein said fluid distribution layer extends over a surface smaller than a surface of the absorbent pad that faces the fluid distribution layer.

7. The dressing according to claim 1, wherein said fluid distribution layer extends over an entire surface of the absorbent pad that faces the fluid distribution layer.

8. The dressing according to claim 1, wherein said fluid distribution layer extends over an entire surface of the absorbent pad that faces the fluid distribution layer and beyond said surface of the absorbent pad.

9. The dressing according to claim 1 wherein said absorbent material is composed of a material chosen in the group consisting of hydrophilic polyurethane, carboxymethylcellulose fibres, sodium polyacrylate, sodium alginate, carboxymethylcellulose, sodium polyacrylate, sodium alginate, and mixtures thereof.

10. The dressing according to claim 1, wherein said perforated reinforcement is a perforated knit, a unitary net made of thermoplastic material, a perforated film or a perforated nonwoven.

11. The dressing according to claim 1, wherein said adhesive is a hydrogel, a pressure-sensitive adhesive (PSA) or a silicone-based adhesive.

12. The dressing according to claim 1, wherein the total weight of adhesive on all of both faces of the perforated reinforcement is between 30 $g/m^2$ and 500 $g/m^2$.

13. The dressing according to claim 1, wherein the perforated reinforcement has an opening rate between 5% and 50%.

14. The dressing according to claim 1, wherein the absorbent pad consists of a material chosen in the group consisting of hydrophilic polyurethane foams, absorbent nonwoven materials based on carboxymethylcellulose fibres or sodium alginate, composites based on porous nonwoven materials comprising sandwiched absorbent materials and sachets containing absorbent materials.

\* \* \* \* \*